US010085635B2

(12) United States Patent
Liu

(10) Patent No.: US 10,085,635 B2
(45) Date of Patent: Oct. 2, 2018

(54) INFORMATION PROCESSING METHOD AND WEARABLE ELECTRONIC DEVICE

(71) Applicants: Beijing Lenovo Software Ltd., Beijing (CN); LENOVO (BEIJING) LIMITED, Beijing (CN)

(72) Inventor: Zheng Liu, Beijing (CN)

(73) Assignees: Beijing Lenovo Software Ltd., Beijing (CN); LENOVO (BEIJING) LIMITED, Beijing (CN)

(*) Notice: Subject to any disclaimer, the term of this patent is extended or adjusted under 35 U.S.C. 154(b) by 208 days.

(21) Appl. No.: 14/577,282

(22) Filed: Dec. 19, 2014

(65) Prior Publication Data
US 2015/0374230 A1 Dec. 31, 2015

(30) Foreign Application Priority Data
Jun. 30, 2014 (CN) .......................... 2014 1 0306886

(51) Int. Cl.
A61B 3/10 (2006.01)
A61B 3/11 (2006.01)
A61B 3/14 (2006.01)

(52) U.S. Cl.
CPC .............. A61B 3/112 (2013.01); A61B 3/14 (2013.01)

(58) Field of Classification Search
CPC ........ G02C 11/10; G02C 7/083; G02C 7/104; A61B 3/0008; A61B 3/0083; A61B 3/112; A61B 3/14; A61B 3/145; A61B 3/024; A61B 3/12; A61B 3/103; A61B 3/107; A61B 3/113; A61B 3/0091; A61B 3/0093; A61B 3/017; A61B 3/032; G02B 27/26; G02B 27/017; G02B 27/0172; G02B 27/0101; G02B 27/0093; G02B 27/2264; H04N 13/044; H04N 13/0484
USPC ....... 351/158, 204, 205, 206, 211, 246, 210, 351/239, 243; 359/275, 319, 630; 349/1, 349/11, 193; 348/78
See application file for complete search history.

(56) References Cited

U.S. PATENT DOCUMENTS 7,744,216 B1 6/2010 Uhlhorn
8,752,963 B2 6/2014 McCulloch et al.
(Continued)

FOREIGN PATENT DOCUMENTS

CN 101620321 A 1/2010
CN 201489219 U 5/2010
(Continued)

OTHER PUBLICATIONS

Office Action issued in corresponding German Application No. 10 2014 119 225.7 dated Aug. 19, 2015 (6 pages).
(Continued)

Primary Examiner — Mustak Choudhury
(74) Attorney, Agent, or Firm — Osha Liang LLP

(57) ABSTRACT

An information processing method performed in a wearable electronic device, periodically acquiring an eye pupil sizes of a user wearing the wearable electronic device; determining a difference between the eye pupil size acquired in a current cycle and the eye pupil size acquired in a previous cycle; and adjusting an optical characteristics of a light transmission module of the wearable electronic device according to the determined difference between the eye pupil size acquired in a current cycle and the eye pupil size acquired in a previous cycle.

11 Claims, 5 Drawing Sheets

(56) References Cited

U.S. PATENT DOCUMENTS

| | | | | |
|---|---|---|---|---|
| 2011/0176106 A1* | 7/2011 | Lewkowski | ........... | A61B 3/112 |
| | | | | 351/206 |
| 2013/0027655 A1* | 1/2013 | Blum | ..................... | G02C 7/083 |
| | | | | 349/193 |
| 2013/0114043 A1* | 5/2013 | Balan | ................... | H04N 13/044 |
| | | | | 351/210 |
| 2015/0370071 A1* | 12/2015 | Alton | ................. | G02B 27/0172 |
| | | | | 349/11 |

FOREIGN PATENT DOCUMENTS

| | | | |
|---|---|---|---|
| CN | 103091843 A | 5/2013 | |
| CN | 103885206 A | 6/2014 | |
| EP | 2499960 A1 | 9/2012 | |

OTHER PUBLICATIONS

Office Action issued in corresponding Chinese Application No. 201410306886.2 dated Sep. 21, 2016, and English translation thereof (16 pages).

Office Action issued in corresponding Chinese Application No. 201410306886.2 dated Jan. 25, 2016, and English translation thereof (18 pages).

* cited by examiner

INFORMATION PROCESSING METHOD AND WEARABLE ELECTRONIC DEVICE

CROSS-REFERENCE TO RELATED APPLICATION(S)

This application claims priority to Chinese Application No. 201410306886.2, filed on Jun. 30, 2014, which is incorporated herein by reference in its entirety.

TECHNICAL FIELD

The present disclosure relates to a field of computer technology, and in particular, to an information processing method and a wearable electronic device.

BACKGROUND

With the evolution of science and technology, electronic technology has been rapidly developed. More and more types of electronic products are available, which enables people to enjoy various conveniences brought by the development of science and technology. Now, people may enjoy comfortable lives brought by the development of science and technology by using various types of electronic devices, such as wearable electronic devices.

Wearable electronic devices, such as wearable glasses (also referred to as smart glasses), may have functions of e.g. taking pictures and videos etc.

SUMMARY

An aspect of the present disclosure provides an information processing method applied to a wearable electronic device. The wearable electronic device comprises a fixed portion configured to maintain a relative position relationship between the wearable electronic device and a head of a user when the user wears the electronic device. The fixed portion is connected to a light transmission module and an image collection unit. The light transmission module is provided with first material. The method comprises steps of: obtaining human eye characteristic information of the user collected by the image collection unit; determining a first control strategy according to the human eye characteristic information and a first preset rule; and changing optical characteristics of the first material according to the first control strategy, so as to adjust optical parameters of the light transmission module.

Preferably, the step of obtaining the human eye characteristic information of the user collected by the image collection unit comprises controlling the image collection unit to collect eye pupil characteristic information of the user.

Preferably, the first material is a liquid crystal. Accordingly, the step of determining the first control strategy according to the human eye characteristic information and the first preset rule comprises steps of: determining a variation amplitude of the eye pupil according to the eye pupil characteristic information; judging whether the variation amplitude of the eye pupil matches with a first preset condition or a second preset condition; determining that the first control strategy is to increase a driving voltage of the liquid crystal to a first specified parameter in the case that the variation amplitude of the eye pupil matches with the first preset condition, and determining that the first control strategy is to decrease the driving voltage of the liquid crystal to a second specified parameter in the case that the variation amplitude of the eye pupil matches with the second preset condition, wherein the first preset condition indicates that the variation amplitude of the eye pupil is larger than a first preset value, and the second preset condition indicates that the variation amplitude of the eye pupil is larger than a second preset value.

Preferably, the step of changing the optical characteristics of the first material according to the first control strategy comprises steps of: adjusting the driving voltage of the liquid crystal according to the first control strategy; and changing an arrangement direction of liquid crystal molecules in the liquid crystal according to the adjusted driving voltage, so as to adjust a polarization direction of the liquid crystal, and thus to adjust a light transmittance and color of the light transmission module.

Preferably, the light transmittance comprises a transmittance of at least one visible light.

Preferably, the method further comprises steps of: recording a time when the first control strategy is determined; calculating a time difference according to the time when the first control strategy is determined and the time when the first control strategy was determined previously; and performing no operation in the case that the time difference is less than a preset period.

Preferably, the fixed portion is further provided with a light collection unit. The method further comprises a step of: obtaining light information, collected by the light collection unit, of an environment where the wearable electronic device is located. The step of determining the first control strategy according to the human eye characteristic information and the first preset rule comprises determining the first control strategy according to the human eye characteristic information, the light information and the first preset rule.

Another aspect of the present disclosure provides a wearable electronic device. The wearable electronic device comprises an image collection unit configured to collect human eye characteristic information of a user. The image collection unit is connected to a fixed portion. The fixed portion is configured to maintain a relative position relationship between the wearable electronic device and a head of the user when the user wears the electronic device. The wearable electronic device further comprises an application processing unit. The application processing unit is configured to: obtain the human eye characteristic information of the user collected by the image collection unit; determine a first control strategy cording to the human eye characteristic information and a first preset rule; and change optical characteristics of first material according to the first control strategy, so as to adjust optical parameters of a light transmission module, wherein the light transmission module is connected to the fixed portion, and the light transmission module is provided with the first material.

Preferably, the application processing unit is further configured to control the image collection unit to collect eye pupil characteristic information of the user.

Preferably, the first material is a liquid crystal. The application processing unit is further configured to: determining a variation amplitude of the eye pupil according to the eye pupil characteristic information; judging whether the variation amplitude of the eye pupil matches with a first preset condition or a second preset condition; determining that the first control strategy is to increase a driving voltage of the liquid crystal to a first specified parameter in the case that the variation amplitude of the eye pupil matches with the first preset condition, and determining that the first control strategy is to decrease the driving voltage of the liquid crystal to a second specified parameter in the case that the variation amplitude of the eye pupil matches with the second preset condition, wherein the first preset condition indicates that the variation amplitude of the eye pupil is larger than a first preset value, and the second preset condition indicates that the variation amplitude of the eye pupil is larger than a second preset value.

Preferably, the application processing unit is further configured to adjust the driving voltage of the liquid crystal according to the first control strategy; and change an arrangement direction of liquid crystal molecules in the liquid crystal according to the adjusted driving voltage, so as to adjust a polarization direction of the liquid crystal, and thus to adjust a light transmittance and color of the light transmission module.

Preferably, the light transmittance comprises a transmittance of at least one visible light.

Preferably, the application processing unit is further configured to: record a time when the first control strategy is determined; calculate a time difference according to the time when the first control strategy is determined and the time when the first control strategy was determined previously; and perform no operation in the case that the time difference is less than a preset period.

Preferably, the wearable electronic device further comprises a light collection unit arranged on the fixed portion. The light collection unit is configured to collect light information of an environment where the wearable electronic device is located. And, the application processing unit is further configured to: obtain the light information, collected by the light collection unit, of the environment where the wearable electronic device is located; and determine the first control strategy according to the human eye characteristic information, the light information and the first preset rule.

DETAILED DESCRIPTION OF THE EMBODIMENTS

Hereinafter, the present disclosure will be described in detail in connection with the drawings and particular embodiments.

First Method Example

Figure 1:
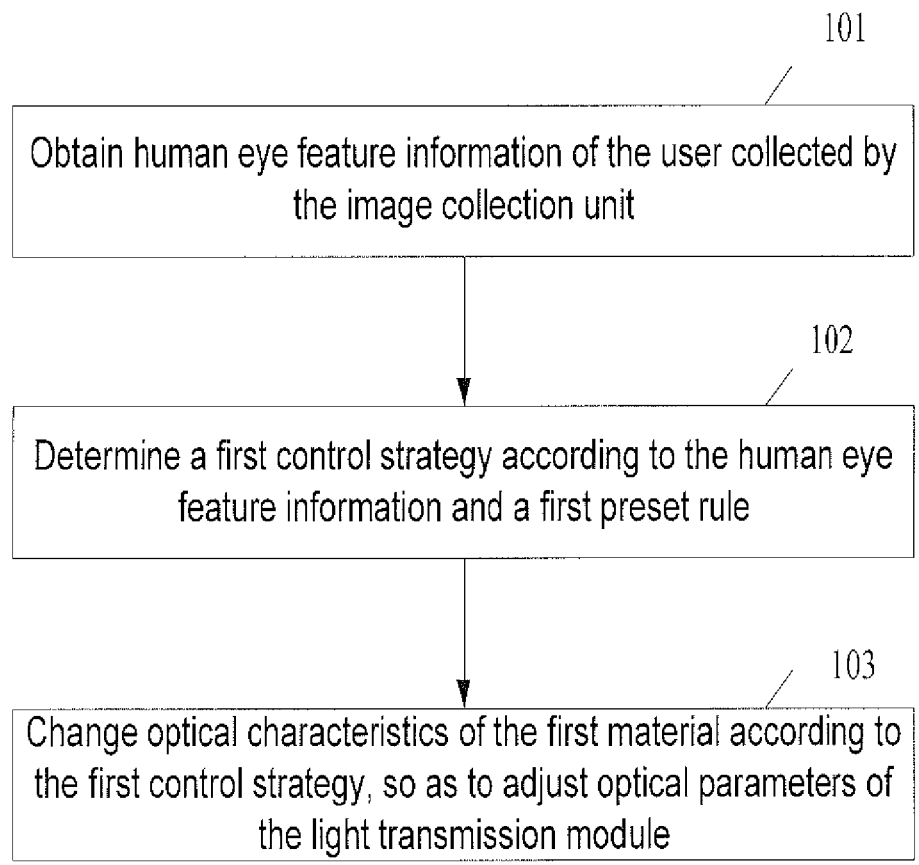
FIG. 1 is a first exemplary flowchart of an information processing method according to an embodiment of the present disclosure.

An embodiment of the present disclosure provides an information processing method applied to a wearable electronic device. The wearable electronic device comprises a fixed portion configured to maintain a relative position relationship between the wearable electronic device and a head of a user when the user wears the electronic device. The fixed portion is connected to a light transmission module and an image collection unit. The light transmission module is provided with first material. As shown in FIG. 1, the method comprises:

Step 101 of obtaining human eye characteristic information of the user collected by the image collection unit;

Step 102 of determining a first control strategy according to the human eye characteristic information and a first preset rule; and Step 103 of changing optical characteristics of the first material according to the first control strategy, so as to adjust optical parameters of the light transmission module.

Here, the wearable electronic device may be smart glasses. The fixed portion may be a frame of glasses.

The image collection unit may be a camera.

Figure 2:
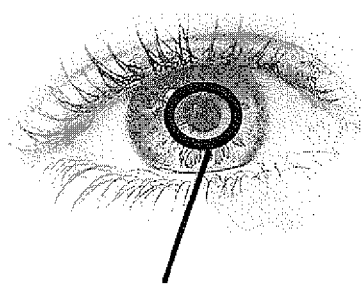
FIG. 2 is a schematic diagram of a pupil of a human eye.

Said collecting the human eye characteristic information of the user may comprise: periodically capturing, by the image collection unit, an image in a specified area; and collecting, by the image collection unit, eye pupil characteristic information of the user in the image of the specified area, e.g. as shown in FIG. 2, collecting variation information of the pupil 21 of the user's eye. The periodicity may be set according to actual requirements, e.g. once per second. The eye pupil characteristic information may be a diameter, a radius, or an area of the pupil 21.

The step of determining the first control strategy according to the human eye characteristic information and the first preset rule may comprise: determining a variation amplitude of the eye pupil according to the human eye characteristic information collected in the present cycle and the human eye characteristic information collected in the previous cycle; and adjusting the light transmission module by using the first rule and the determined variation amplitude of the eye pupil, wherein adjustment parameters are taken as the first control strategy.

A scenario in which the present embodiment is implemented will be described below.

The image of the specific area may be collected by the camera;

the human eye characteristic of the user, i.e., the diameter or radius or area of the pupil, may be collected according to the image of the specified area;

the first control strategy may be determined according to the human eye characteristic information and the first preset rule;

the optical characteristics of the first material may be changed according to the first control strategy, so as to adjust the optical parameters of the light transmission module by adjusting the optical characteristics of the first material.

Therefore, with the technical solution of the present embodiment, the first control strategy may be determined according to the human eye characteristic information of the user; the optical characteristics of the first material may be changed according to the first control strategy, and accordingly the optical parameters of the light transmission module may be adjusted. Thus, the sensitivity of the user's eyes to the light may be determined according to the situation of the user, so that the eyes of the user may obtain suitable light, and the use experience of the user may thus be improved.

Second Method Example

Figure 3:
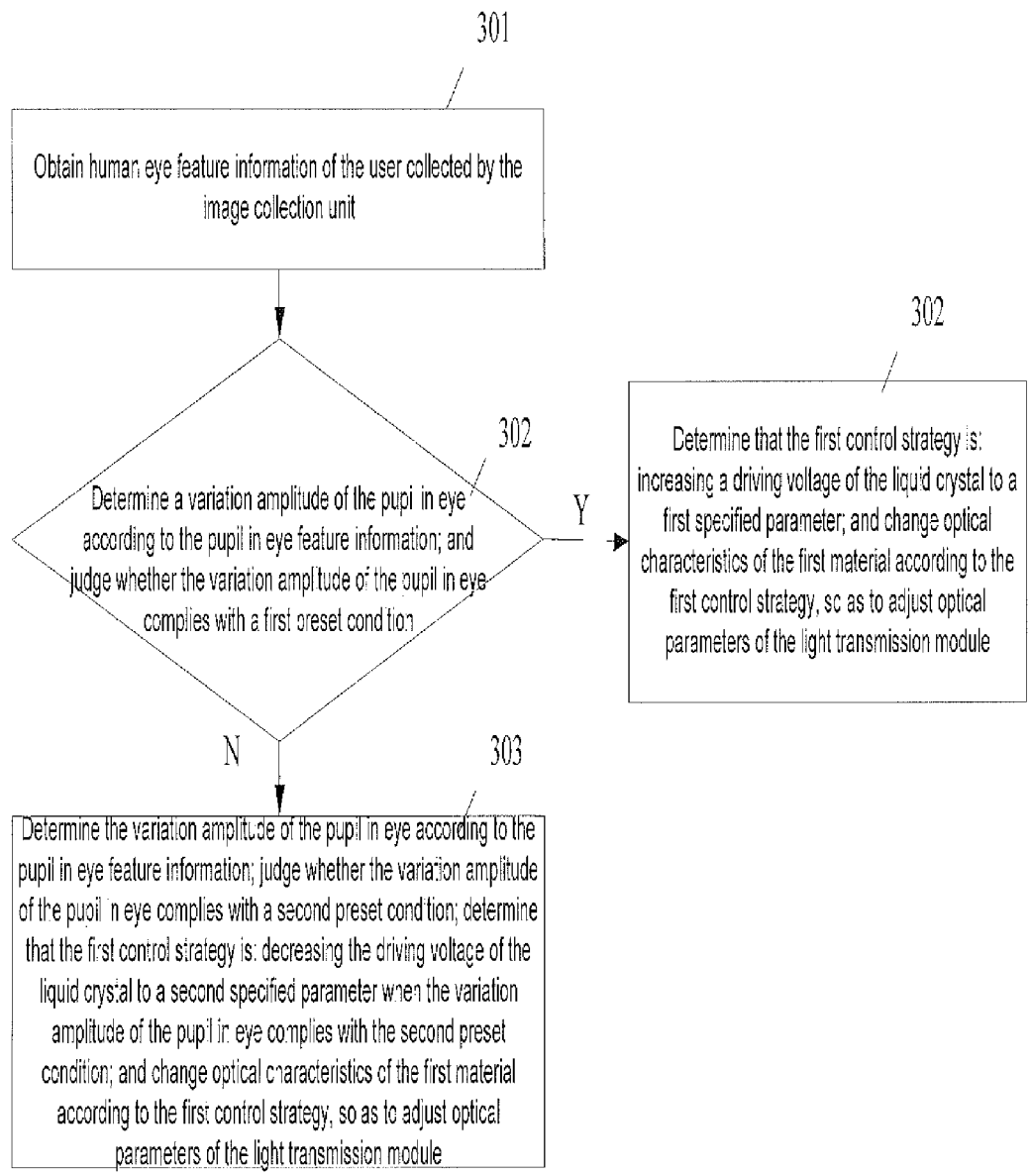
FIG. 3 is a second exemplary flowchart of an information processing method according to an embodiment of the present disclosure.

An embodiment of the present disclosure provides an information processing method applied to a wearable electronic device. The wearable electronic device comprises: a fixed portion configured to maintain a relative position relationship between the wearable electronic device and a head of a user when the user wears the electronic device. The fixed portion is connected to a light transmission module and an image collection unit. The light transmission module is provided with first material. The first material is a liquid crystal. As shown in FIG. 3, the method may comprises:

Step 301 of obtaining human eye characteristic information of the user collected by the image collection unit;

Step 302 of determining a variation amplitude of the eye pupil according to the eye pupil characteristic information; judging whether the variation amplitude of the eye pupil matches with a first preset condition; and determining that the first control strategy is to increase a driving voltage of the liquid crystal to a first specified parameter in the case that the variation amplitude of the eye pupil matches with the first preset condition; changing optical characteristics of the first material according to the first control strategy, so as to adjust optical parameters of the light transmission module; otherwise, proceeding to Step 303;

Step 303 of determining the variation amplitude of the eye pupil according to the eye pupil characteristic information; judging whether the variation amplitude of the eye pupil matches with a second preset condition; and determining that the first control strategy is to decrease the driving voltage of the liquid crystal to a second specified parameter win the case that the variation amplitude of the eye pupil matches with the second preset condition; changing optical characteristics of the first material according to the first control strategy, so as to adjust optical parameters of the light transmission module; wherein the first preset condition indicates that the variation amplitude of the eye pupil is larger than a first preset value, and the second preset condition indicates that the variation amplitude of the eye pupil is larger than a second preset value.

Here, the wearable electronic device may be smart glasses. The fixed portion may be a frame of glasses.

The image collection unit may be a camera.

The above Steps 302 and 303 can be performed in an arbitrary order. As will be understood by the skilled in the art, when Step 303 is performed firstly, Step 302 may be performed when it is determined that the second preset condition is not satisfied.

Collecting the human eye characteristic information of the user may comprise: periodically capturing, by the image collection unit, an image in a specified area; collecting, by the image collection unit, eye pupil characteristic information of the user in the image of the specified area, e.g. as shown in FIG. 2, collecting variation information of the pupil 21 of the user's eye. The periodicity may be set according to actual requirements, e.g. once per second. The eye pupil characteristic information may be a diameter, a radius, or an area of the pupil 21.

The step of determining the variation amplitude of the eye pupil according to the eye pupil characteristic information may comprise: calculating a difference value between the value of the eye pupil characteristic information collected in the present cycle and the value of the eye pupil characteristic information collected in the previous cycle, and taking the difference value as the variation amplitude of the eye pupil.

A scenario in which the present embodiment is implemented will be described below.

The image of the specific area may be collected by the camera;

the human eye feature of the user, i.e., the diameter or radius or area of the pupil, may be collected according to the image of the specified area;

the variation amplitude of the eye pupil is determined according to the eye pupil characteristic information;

the first control strategy is determined as increasing the driving voltage of the liquid crystal to the first specified parameter, in the case that the variation amplitude of the eye pupil is zoom-in and the zoom-in amplitude matches with the first preset condition;

the optical characteristics of the liquid crystal is changed according to the first control strategy so as to adjust the optical parameters of the light transmission module by adjusting the optical characteristics of the first material.

Therefore, with the technical solution of the present embodiment, the first control strategy may be determined according to the human eye characteristic information of the user; the optical characteristics of the first material may be changed according to the first control strategy, and accordingly the optical parameters of the light transmission module may be adjusted. Thus, the sensitivity of the user's eyes to the light may be determined according to the situation of the user, so that the eyes of the user may obtain suitable light, and the use experience of the user may thus be improved.

Third Method Example

Figure 4:
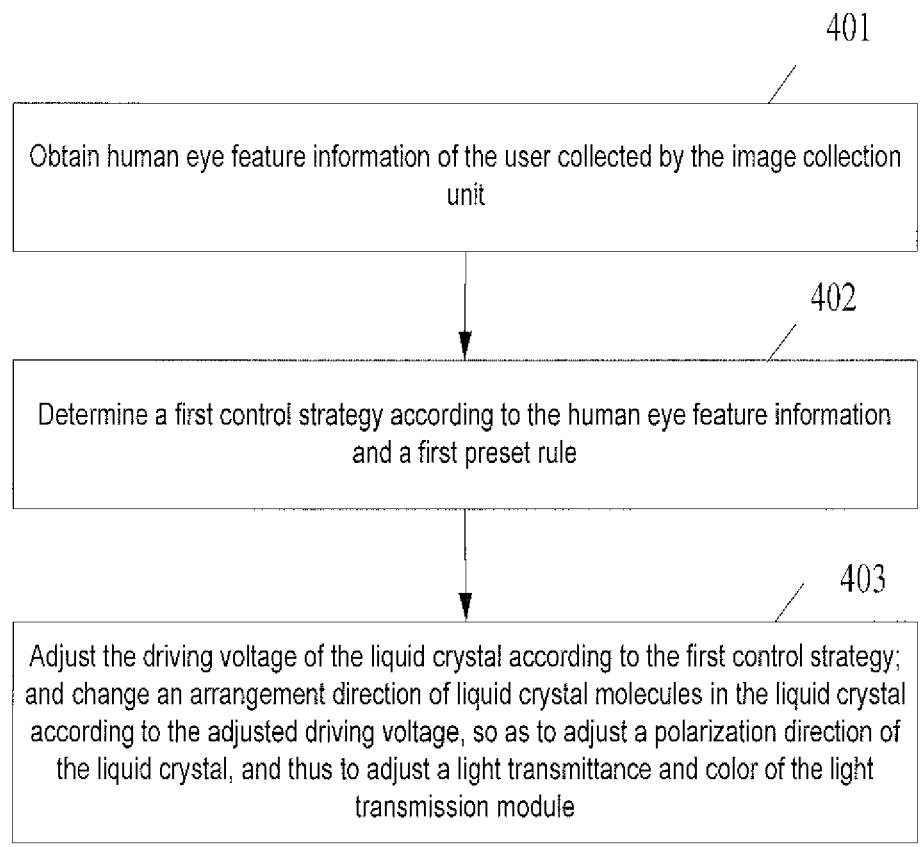
FIG. 4 is a third exemplary flowchart of an information processing method according to an embodiment of the present disclosure.

An embodiment of the present disclosure provides an information processing method applied to a wearable electronic device. The wearable electronic device comprises a fixed portion configured to maintain a relative position relationship between the wearable electronic device and a head of a user when the user wears the electronic device. The fixed portion is connected to a light transmission module and an image collection unit. The light transmission module is provided with first material, the first material is a liquid crystal. As shown in FIG. 4, the method comprises:

Step 401 of obtaining human eye characteristic information of the user collected by the image collection unit;

Step 402 of determining a first control strategy according to the human eye characteristic information and a first preset rule; and Step 403 of adjusting the driving voltage of the liquid crystal according to the first control strategy; and changing an arrangement direction of liquid crystal molecules in the liquid crystal according to the adjusted driving voltage, so as to adjust a polarization direction of the liquid crystal, and thus to adjust a light transmittance and color of the light transmission module.

Here, the wearable electronic device may be smart glasses. The fixed portion may be a frame of glasses.

The image collection unit may be a camera.

Collecting the human eye characteristic information of the user may comprise: periodically capturing, by the image collection unit, an image in a specified area; collecting, by the image collection unit, eye pupil characteristic information of the user in the image of the specified area, e.g. as shown in FIG. 2, collecting variation information of the pupil 21 of the user's eye. The periodicity may be set according to actual requirements, e.g. once per second. The eye pupil characteristic information may be a diameter, a radius, or an area of the pupil 21.

The step of determining the first control strategy according to the human eye characteristic information and the first preset rule may comprise:

determining a variation amplitude of the eye pupil according to the eye pupil characteristic information; judging whether the variation amplitude of the eye pupil matches with a first preset condition; and determining that the first control strategy is to increase a driving voltage of the liquid crystal to a first specified parameter in the case that the variation amplitude of the eye pupil matches with the first preset condition, wherein the first specified parameter may be an alternating voltage.

determining the variation amplitude of the eye pupil according to the eye pupil characteristic information; judging whether the variation amplitude of the eye pupil matches with a second preset condition; and determining that the first control strategy is to decrease the driving voltage of the liquid crystal to a second specified parameter in the case that the variation amplitude of the eye pupil matches with the second preset condition, wherein the second specified parameter may be a 0 voltage;

wherein the first preset condition indicates that the variation amplitude of the eye pupil is larger than a first preset value, and the second preset condition indicates that the variation amplitude of the eye pupil is larger than a second preset value.

The step of determining the variation amplitude of the eye pupil according to the eye pupil characteristic information may comprises: calculating a difference value between the value of the eye pupil characteristic information collected in the present cycle and the value of the eye pupil characteristic information collected in the previous cycle, and taking the difference value as the variation amplitude of the eye pupil.

Figure 5A:
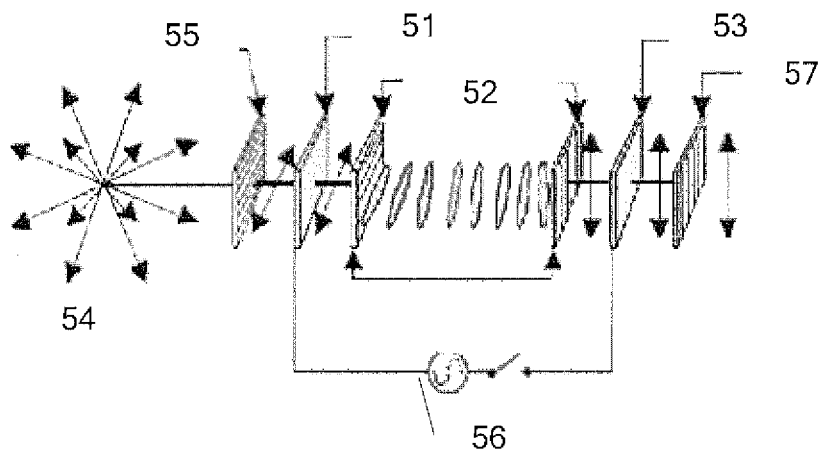
FIG. 5a is a first schematic diagram of controlling an arrangement direction of liquid crystal molecules in a first portion by a driving voltage according to an embodiment of the present disclosure.
Figure 5B:
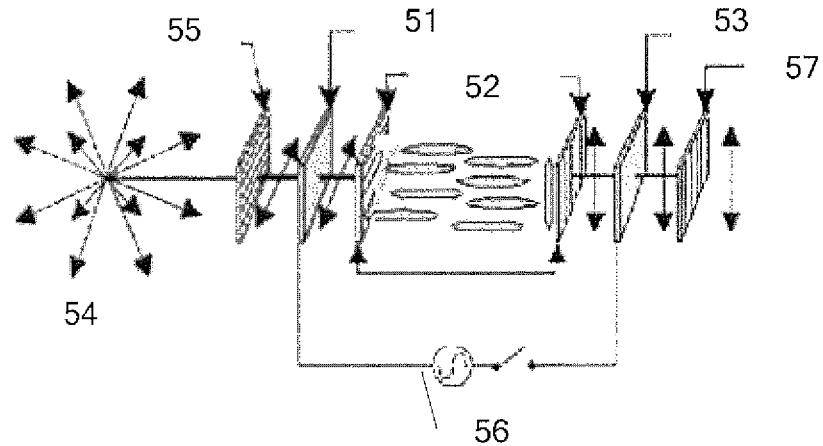
FIG. 5b is a second schematic diagram of controlling an arrangement direction of liquid crystal molecules in a first portion by a driving voltage according to an embodiment of the present disclosure.

As shown in FIGS. 5a and 5b, the light transmission module may comprise: a first layer light transmission part, first material a second layer light transmission part. The first material may be liquid crystal, and may particularly comprise liquid crystal molecular coating layers 52 and liquid crystal molecules.

The arrangement direction of liquid crystal molecules in the liquid crystal may be changed according to the adjusted driving voltage, so as to adjust the polarization direction of the liquid crystal. Thus, the light transmittance and color of the light transmission module may be adjusted as shown in FIGS. 5a and 5b. In particular, electrodes of a liquid crystal panel are made of a metallic compound such as ITO, formed on both sides of a substrate made of the first material and etched by an etching process. The first layer light transmission part may comprise a first polarizer 55 and a first glass substrate 51. The second layer light transmission part may comprise a second polarizer 57 and a second glass substrate 53.

As shown in FIG. 5a, the arrangement of the liquid crystal molecules is a helical structure having an optical rotation activity for light. Polarization directions of the first polarizer 55 and the second polarizer 57 at the two sides are perpendicular with each other. When the voltage between the upper and the lower substrates is 0, only light in a direction identical with that of the first polarizer 55 may enter into the coating layer of the liquid crystal molecules in the helical structure upon natural light 54 goes through the first polarizer 55. The direction of the incident light is rotated by 90° due to the optical rotation activity of the helical structure. Then, the rotated incident light is irradiated to the second polarizer 57 on the other end. Since the polarization directions of the two polarizers are perpendicular with each other, the incident light may completely go out through the polarizer at the other end, and thus completely enter into the user's eyes. The user may see the color of the first polarizer or the second polarizer. For example, when both the first polarizer and the second polarizer are transparent, the user may see the natural light.

As shown in FIG. 5b, when the voltage 56 between the first glass substrate 51 and the second glass substrate 53 is an alternating voltage, the helical structure of the liquid crystal molecules in the first material may become a syntropic arrangement under the effect of an electric (magnetic) field, and thus does not have any rotation on the direction of the light. Since the polarization directions of the first polarizer 55 and the second polarizer 57 are perpendicular with each other, the incident light cannot go out through the second polarizer 57, and no light 54 can enter into the user's eyes. Then the user may see a black color. As such, two basic bright and dark states of the liquid crystal display may be implemented by applying different alternating voltages across the electrodes of the upper and the lower glass substrates.

The light transmittance comprises a transmittance of at least one visible light, e.g., a transmittance of natural light.

A scenario in which the present embodiment is implemented will be described below.

The image of the specific area may be collected by the camera;

the human eye feature of the user, i.e., the diameter or radius or area of the pupil, may be collected according to the image of the specified area;

the variation amplitude of the eye pupil is determined according to the eye pupil characteristic information;

the first control strategy is determined as increasing the driving voltage of the liquid crystal to the first specified parameter, when the variation amplitude of the eye pupil is zoom-in and the zoom-in amplitude matches with the first preset condition;

the optical characteristics of the liquid crystal is changed according to the first control strategy, so as to adjust the optical parameters of the light transmission module by adjusting the optical characteristics of the first material.

Therefore, with the technical solution of the present embodiment, the first control strategy may be determined according to the human eye characteristic information of the user; the optical characteristics of the first material may be changed according to the first control strategy, and accordingly the optical parameters of the light transmission module may be adjusted. Thus, the sensitivity of the user's eyes to the light may be determined according to the situation of the user, so that the eyes of the user may obtain suitable light, and the use experience of the user may thus be improved.

Fourth Method Example

Figure 6:
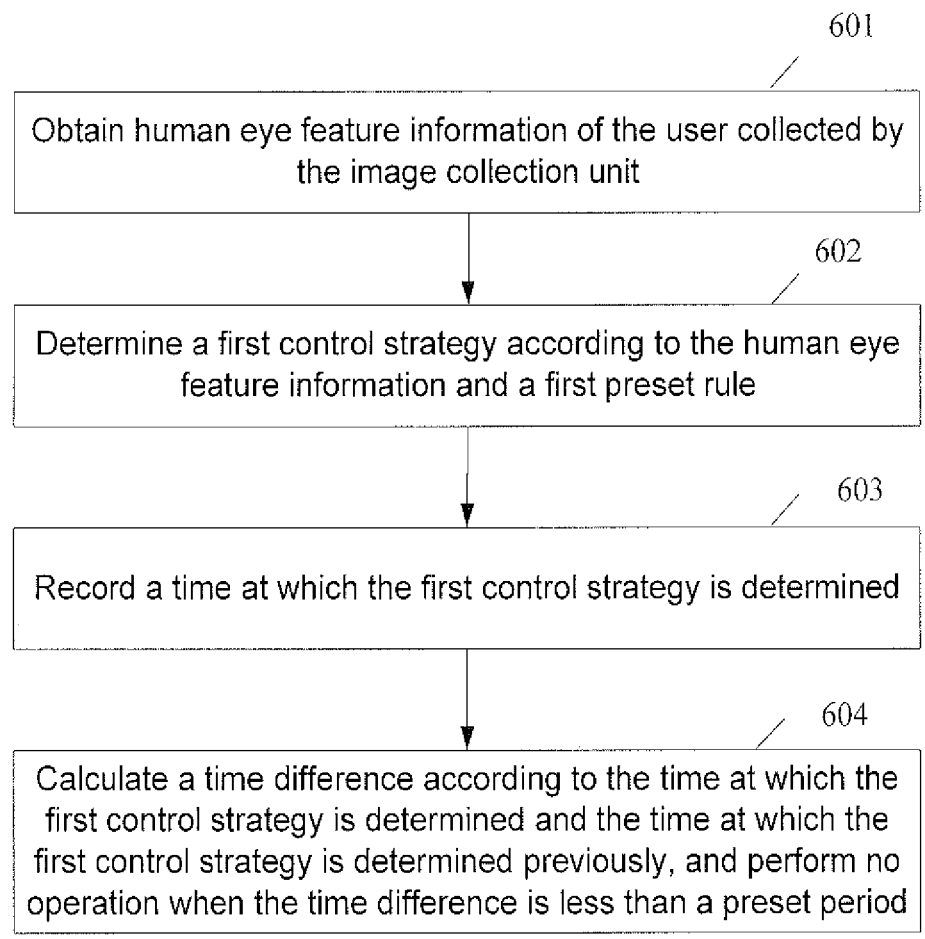
FIG. 6 is a fourth exemplary flowchart of an information processing method according to an embodiment of the present disclosure.

An embodiment of the present disclosure provides an information processing method applied to a wearable electronic device. The wearable electronic device comprises a fixed portion configured to maintain a relative position relationship between the wearable electronic device and a head of a user when the user wears the electronic device. The fixed portion is connected to a light transmission module and an image collection unit. The light transmission module is provided with first material. The first material is liquid crystal. As shown in FIG. 6, the method comprises:

Step 601 of obtaining human eye characteristic information of the user collected by the image collection unit;

Step 602 of determining a first control strategy according to the human eye characteristic information and a first preset rule;

Step 603 of recording a time when the first control strategy is determined;

Step 604 of calculating a time difference according to the time when the first control strategy is determined and the time when the first control strategy was determined previously; and performing no operation and ending the process in the case that the time difference is less than a preset period.

Preferably, when the time difference is no less than the preset period, the driving voltage of the liquid crystal is adjusted according to the first control strategy; the arrangement direction of the liquid crystal molecules in the liquid crystal is changed according to the adjusted driving voltage, so as to adjust the polarization direction of the liquid crystal, and thus to adjust the light transmittance and the color of the light transmission module.

Here, the wearable electronic device may be smart glasses. The fixed portion may be a frame of glasses.

The image collection unit may be a camera.

Collecting the human eye characteristic information of the user may comprise: periodically capturing, by the image collection unit, an image in a specified area; collecting, by the image collection unit, eye pupil characteristic information of the user in the image of the specified area, as shown in FIG. 2, collecting variation information of the pupil 21 of the user's eye. The periodicity may be set according to actual requirements, e.g. once per second. The eye pupil characteristic information may be a diameter, a radius, or an area of the pupil 21.

The step of determining the variation amplitude of the eye pupil according to the eye pupil characteristic information may comprise:

determining a variation amplitude of the eye pupil according to the eye pupil characteristic information; judging whether the variation amplitude of the eye pupil matches with a first preset condition; and determining that the first control strategy is to increase a driving voltage of the liquid crystal to a first specified parameter in the case that the variation amplitude of the eye pupil matches with the first preset condition, wherein the first specified parameter may be an alternating voltage.

determining the variation amplitude of the eye pupil according to the eye pupil characteristic information; judging whether the variation amplitude of the eye pupil matches with a second preset condition; and determining that the first control strategy is to decrease the driving voltage of the liquid crystal to a second specified parameter in the case that the variation amplitude of the eye pupil matches with the second preset condition, wherein the second specified parameter may be a 0 voltage;

wherein the first preset condition indicates that the variation amplitude of the eye pupil is larger than a first preset value, and the second preset condition indicates that the variation amplitude of the eye pupil is larger than a second preset value.

The step of determining the variation amplitude of the eye pupil according to the eye pupil characteristic information may comprises: calculating a difference value between the value of the eye pupil characteristic information collected in the present cycle and the value of the eye pupil characteristic information collected in the previous cycle, and taking the difference value as the variation amplitude of the eye pupil.

As shown in FIGS. 5a and 5b, the light transmission module may comprise: a first layer light transmission part, first material a second layer light transmission part. The first material may be liquid crystal, and may particularly comprise liquid crystal molecular coating layers 52 and liquid crystal molecules.

The arrangement direction of liquid crystal molecules in the liquid crystal may be changed according to the adjusted driving voltage, so as to adjust the polarization direction of the liquid crystal. Thus, the light transmittance and color of the light transmission module may be adjusted as shown in FIGS. 5a and 5b. In particular, electrodes of a liquid crystal panel are made of a metallic compound such as ITO formed on both sides of a substrate made of the first material and etched by an etching process. The first layer light transmission part may comprise a first polarizer 55 and a first glass substrate 51. The second layer light transmission part may comprise a second polarizer 57 and a second glass substrate 53.

As shown in FIG. 5a, the arrangement of the liquid crystal molecules is a helical structure having an optical rotation activity for light. Polarization directions of the first polarizer 55 and the second polarizer 57 at the two sides are perpendicular with each other. When the voltage between the upper and the lower substrates is 0, only light in a direction identical with that of the first polarizer 55 may enter into the coating layer of the liquid crystal molecules in the helical structure upon natural light 54 goes through the first polarizer 55. The direction of the incident light is rotated by 90° due to the optical rotation activity of the helical structure. Then, the rotated incident light is irradiated to the second polarizer 57 on the other end. Since the polarization directions of the two polarizers are perpendicular with each other, the incident light may completely go out through the polarizer at the other end, and thus completely enter into the user's eyes. The user may see the color of the first polarizer or the second polarizer. For example, when both the first polarizer and the second polarizer are transparent, the user may see the natural light.

As shown in FIG. 5b, when the voltage 56 between the first glass substrate 51 and the second glass substrate 53 is an alternating voltage, the helical structure of the liquid crystal molecules in the first material may become a syntropic arrangement under the effect of an electric (magnetic) field, and thus does not have any rotation on the direction of the light. Since the polarization directions of the first polarizer 55 and the second polarizer 57 are perpendicular with each other, the incident light cannot go out through the second polarizer 57, and no light 54 can enter into the user's eyes. Then the user may see a black color. As such, two basic bright and dark states of the liquid crystal display may be implemented by applying different alternating voltages across the electrodes of the upper and the lower glass substrates.

The light transmittance comprises a transmittance of at least one visible light, e.g., a transmittance of natural light.

A scenario in which the present embodiment is implemented will be described below.

The image of the specific area may be collected by the camera;

the human eye feature of the user, i.e., the diameter or radius or area of the pupil, may be collected according to the image of the specified area;

the variation amplitude of the eye pupil is determined according to the eye pupil characteristic information;

the first control strategy is determined as increasing the driving voltage of the liquid crystal to the first specified parameter, when the variation amplitude of the eye pupil is zoom-in, and the zoom-in amplitude matches with the first preset condition;

recording the time when the first control strategy is determined, and calculating the time difference according to the time when the first control strategy is determined and the time when the first control strategy is determined previously, and performing no operation when the time difference is less than the preset period; as such, the light transmittance of the glasses may be avoided from being changed many times within a short time period;

the optical characteristics of the liquid crystal is changed according to the first control strategy, so as to adjust the optical parameters of the light transmission module by adjusting the optical characteristics of the first material, when the time difference is no less than the preset period.

Therefore, with the technical solution of the present embodiment, the first control strategy may be determined according to the human eye characteristic information of the user; the optical characteristics of the first material may be changed according to the first control strategy, and accordingly the optical parameters of the light transmission module may be adjusted. Thus, the sensitivity of the user's eyes to the light may be determined according to the situation of the user, so that the eyes of the user may obtain suitable light, and the use experience of the user may thus be improved.

Fifth Method Example

An embodiment of the present disclosure provides an information processing method applied to a wearable electronic device. The wearable electronic device comprises a fixed portion configured to maintain a relative position relationship between the wearable electronic device and a head of a user when the user wears the electronic device. The fixed portion is connected to a light transmission module and an image collection unit. The light transmission module being provided with first material. The first material is liquid crystal. As shown in FIG. 6, the method comprises:

Step 601 of obtaining human eye characteristic information of the user collected by the image collection unit;

Step 602 of determining a first control strategy according to the human eye characteristic information and a first preset rule;

Step 603 of recording a time when the first control strategy is determined;

Step 604 of calculating a time difference according to the time when the first control strategy is determined and the time when the first control strategy is determined previously; and performing no operation in the case that the time difference is less than a preset period.

In addition, when the time difference is no less than the preset period, the driving voltage of the liquid crystal is adjusted according to the first control strategy; the arrangement direction of the liquid crystal molecules in the liquid crystal is changed according to the adjusted driving voltage, so as to adjust the polarization direction of the liquid crystal, and thus to adjust the light transmittance and the color of the light transmission module.

Here, the wearable electronic device may be smart glasses. The fixed portion may be a frame of glasses.

The image collection unit may be a camera.

Collecting the human eye characteristic information of the user may comprise: periodically capturing, by the image collection unit, an image in a specified area; collecting, by the image collection unit, eye pupil characteristic information of the user in the image of the specified area, as shown in FIG. 2, collecting variation information of the pupil 21 of the user's eye. The periodicity may be set according to actual requirements, e.g. once per second. The eye pupil characteristic information may be a diameter, a radius, or an area of the pupil 21.

The step of determining the variation amplitude of the eye pupil according to the eye pupil characteristic information may comprise:

determining a variation amplitude of the eye pupil according to the eye pupil characteristic information; judging whether the variation amplitude of the eye pupil matches with a first preset condition; and determining that the first control strategy is to increase a driving voltage of the liquid crystal to a first specified parameter in the case that the variation amplitude of the eye pupil matches with the first preset condition, wherein the first specified parameter may be an alternating voltage.

determining the variation amplitude of the eye pupil according to the eye pupil characteristic information; judging whether the variation amplitude of the eye pupil matches with a second preset condition; and determining that the first control strategy is to decrease the driving voltage of the liquid crystal to a second specified parameter in the case that the variation amplitude of the eye pupil matches with the second preset condition, wherein the second specified parameter may be a 0 voltage;

wherein the first preset condition indicates that the variation amplitude of the eye pupil is larger than a first preset value, and the second preset condition indicates that the variation amplitude of the eye pupil is larger than a second preset value.

The step of determining the variation amplitude of the eye pupil according to the eye pupil characteristic information may comprises: calculating a difference value between the value of the eye pupil characteristic information collected in the present cycle and the value of the eye pupil characteristic information collected in the previous cycle, and taking the difference value as the variation amplitude of the eye pupil.

As shown in FIGS. 5*a* and 5*b*, the light transmission module may comprise: a first layer light transmission part, first material a second layer light transmission part. The first material may be liquid crystal, and may particularly comprise liquid crystal molecular coating layers 52 and liquid crystal molecules.

The arrangement direction of liquid crystal molecules in the liquid crystal may be changed according to the adjusted driving voltage, so as to adjust the polarization direction of the liquid crystal. Thus, the light transmittance and color of the light transmission module may be adjusted as shown in FIGS. 5*a* and 5*b*. In particular, electrodes of a liquid crystal panel are made of a metallic compound such as ITO, formed on both sides of a substrate made of the first material and etched by an etching process. The first layer light transmission part may comprise a first polarizer 55 and a first glass substrate 51. The second layer light transmission part may comprise a second polarizer 57 and a second glass substrate 53.

As shown in FIG. 5*a*, the arrangement of the liquid crystal molecules is a helical structure having an optical rotation activity for light. Polarization directions of the first polarizer 55 and the second polarizer 57 at the two sides are perpendicular with each other. When the voltage between the upper and the lower substrates is 0, only light in a direction identical with that of the first polarizer 55 may enter into the coating layer of the liquid crystal molecules in the helical structure after natural light 54 goes through the first polarizer 55. The direction of the incident light is rotated by 90° due to the optical rotation activity of the helical structure. Then, the rotated incident light is irradiated to the second polarizer 57 on the other end. Since the polarization directions of the two polarizers are perpendicular with each other, the incident light may completely go out through the polarizer at the other end, and thus completely enter into the user's eyes. The user may see a color of the first polarizer or the second polarizer. For example, when both the first polarizer and the second polarizer are transparent, the user may see the natural light.

As shown in FIG. 5*b*, when the voltage 56 between the first glass substrate 51 and the second glass substrate 53 is an alternating voltage, the helical structure of the liquid crystal molecules in the first material may become a syntropic arrangement under the effect of an electric (magnetic) field, and thus does not have any rotation on the direction of the light. Since the polarization directions of the first polarizer 55 and the second polarizer 57 are perpendicular with each other, the incident light cannot go out through the second polarizer 57, and no light 54 can enter into the user's eyes. Then the user may see a black color. As such, two basic bright and dark states of the liquid crystal display may be implemented by applying different alternating voltages across the electrodes of the upper and the lower glass substrates.

The light transmittance comprises a transmittance of at least one visible light, e.g., a transmittance of natural light.

Preferably, the fixed portion may be further provided with a light collection unit, and the method further comprises steps of:

obtaining light information, collected by the light collection unit, of an environment where the wearable electronic device is located; accordingly, the step of determining the first control strategy according to the human eye characteristic information and the first preset rule comprises: determining the first control strategy according to the human eye characteristic information, the light information and the first preset rule.

The step of determining the first control strategy according to the human eye characteristic information, the light information and the first preset rule may comprises: obtaining brightness or color of the light information; and determining that the first control strategy is to refrain from adjusting the driving voltage according to the brightness of the light information and the first preset rule, in the case that the brightness of the light information is lower than a preset brightness value;

when the brightness of the light information is no lower than the preset brightness value, determining the variation amplitude of the eye pupil according to the eye pupil characteristic information; judging whether the variation amplitude of the eye pupil matches with the first preset condition; and determining that the first control strategy is to increase the driving voltage of the liquid crystal to the first specified parameter, in the case that the variation amplitude of the eye pupil matches with the first preset condition;

determining the variation amplitude of the eye pupil according to the eye pupil characteristic information; judging whether the variation amplitude of the eye pupil matches with the second preset condition; and determining that the first control strategy is to decrease the driving voltage of the liquid crystal to the second specified parameter, in the case that the variation amplitude of the eye pupil matches with the second preset condition;

wherein the first preset condition indicates that the variation amplitude of the eye pupil is larger than the first preset value, and the second preset condition indicates that the variation amplitude of the eye pupil is larger than the second preset value.

Or, determining that the first control strategy is to refrain from adjusting the driving voltage according to the brightness of the light information and the first preset rule, in the case that the color of the light information satisfies a specified color value;

Otherwise, determining the variation amplitude of the eye pupil according to the eye pupil characteristic information; judging whether the variation amplitude of the eye pupil matches with the first preset condition; and determining that the first control strategy is to increase the driving voltage of the liquid crystal to the first specified parameter, in the case that the variation amplitude of the eye pupil matches with the first preset condition;

determining the variation amplitude of the eye pupil according to the eye pupil characteristic information; judging whether the variation amplitude of the eye pupil matches with the second preset condition; and determining that the first control strategy is to decrease the driving voltage of the liquid crystal to the second specified parameter, in the case that the variation amplitude of the eye pupil matches with the second preset condition;

wherein the first preset condition indicates that the variation amplitude of the eye pupil is larger than the first preset value, and the second preset condition indicates that the variation amplitude of the eye pupil is larger than the second preset value.

As such, it may be guaranteed that the user can obtain the largest amount of light when the surrounding light is weaker.

A scenario in which the present embodiment is implemented will be described below.

The image of the specific area may be collected by the camera;

the human eye feature of the user, i.e., the diameter or radius or area of the pupil, may be collected according to the image of the specified area;

the variation amplitude of the eye pupil is determined according to the eye pupil characteristic information;

the first control strategy is determined as increasing the driving voltage of the liquid crystal to the first specified parameter, when the variation amplitude of the eye pupil is zoom-in, and the zoom-in amplitude matches with the first preset condition;

recording the time when the first control strategy is determined, and calculating the time difference according to the time when the first control strategy is determined and the time when the first control strategy is determined previously, and performing no operation when the time difference is less than the preset period; as such, the light transmittance of the glasses may be avoided from being changed many times within a short time period;

the optical characteristics of the liquid crystal is changed according to the first control strategy, so as to adjust the optical parameters of the light transmission module by adjusting the optical characteristics of the first material, when the time difference is no less than the preset period.

Therefore, with the technical solution of the present embodiment, the first control strategy may be determined according to the human eye characteristic information of the user; the optical characteristics of the first material may be changed according to the first control strategy, and accordingly the optical parameters of the light transmission module may be adjusted. Thus, the sensitivity of the user's eyes to the light may be determined according to the situation of the user, so that the eyes of the user may obtain suitable light, and the use experience of the user may thus be improved.

First Device Example

Figure 7:
FIG. 7 is a first structure schematic diagram of a wearable electronic device according to an embodiment of the present disclosure.

An embodiment of the present disclosure provides a wearable electronic device, as shown in FIG. 7, comprising:

an image collection unit 71 connected to a fixed portion, the image collection unit being configured to collect human eye characteristic information of a user; the fixed portion being configured to maintain a relative position relationship between the wearable electronic device and a head of the user when the user wears the electronic device;

an application processing unit 72, configured to obtain the human eye characteristic information of the user collected by the image collection unit; determine a first control strategy according to the human eye characteristic information and a first preset rule; and change optical characteristics of first material according to the first control strategy, so as to adjust optical parameters of the light transmission module; wherein the light transmission module is connected to the fixed portion, and the light transmission module is provided with the first material.

Here, the wearable electronic device may be smart glasses. The fixed portion may be a frame of glasses.

The image collection unit may be a camera.

The application processing unit 72 is particularly configured to periodically capture, by the image collection unit, an image in a specified area; collect eye pupil characteristic information of the user in the image of the specified area, as shown in FIG. 2, collect variation information of the pupil 21 of the user's eye. The periodicity may be set according to actual requirements, e.g. once per second. The eye pupil characteristic information may be a diameter, a radius, or an area of the pupil 21.

The application processing unit 72 is particularly configured to: determine a variation amplitude of the eye pupil according to the human eye characteristic information collected in the present cycle and the human eye characteristic information collected in the previous cycle; and adjust the light transmission module by using the first rule and the determined variation amplitude of the eye pupil, wherein adjustment parameters are taken as the first control strategy.

A scenario in which the present embodiment is implemented will be described below.

The image of the specific area may be collected by the camera;

the human eye characteristics of the user, i.e., the diameter or radius or area of the pupil, may be collected according to the image of the specified area;

the first control strategy may be determined according to the human eye characteristic information and the first preset rule;

the optical characteristics of the first material may be changed according to the first control strategy, so as to adjust the optical parameters of the light transmission module by adjusting the optical characteristics of the first material.

Therefore, with the technical solution of the present embodiment, the first control strategy may be determined according to the human eye characteristic information of the user; the optical characteristics of the first material may be changed according to the first control strategy, and accordingly the optical parameters of the light transmission module may be adjusted. Thus, the sensitivity of the user's eyes to the light may be determined according to the situation of the user, so that the eyes of the user may obtain suitable light, and the use experience of the user may thus be improved.

Second Device Example

An embodiment of the present disclosure provides a wearable electronic device, comprising:

an image collection unit connected to a fixed portion, the image collection unit being configured to collect human eye characteristic information of a user; the fixed portion being configured to maintain a relative position relationship between the wearable electronic device and a head of the user when the user wears the electronic device;

an application processing unit, configured to obtain the human eye characteristic information of the user collected by the image collection unit; determine a first control strategy according to the human eye characteristic information and a first preset rule; and change optical characteristics of first material according to the first control strategy, so as to adjust optical parameters of the light transmission module; wherein the light transmission module is connected to the fixed portion, and the light transmission module is provided with the first material.

Here, the wearable electronic device may be smart glasses. The fixed portion may be a frame of glasses.

The image collection unit may be a camera.

The application processing unit is particularly configured to control the image collection unit to collect eye pupil characteristic information of the user.

The application processing unit is particularly configured to:

determine a variation amplitude of the eye pupil according to the eye pupil characteristic information; judge whether the variation amplitude of the eye pupil matches with a first preset condition; and determine that the first control strategy is to increase a driving voltage of the liquid crystal to a first specified parameter in the case that the variation amplitude of the eye pupil matches with the first preset condition, wherein the first specified parameter may be an alternating voltage;

determine the variation amplitude of the eye pupil according to the eye pupil characteristic information; judge whether the variation amplitude of the eye pupil matches with a second preset condition; and determine that the first control strategy is to decrease the driving voltage of the liquid crystal to a second specified parameter in the case that the variation amplitude of the eye pupil matches with the second preset condition, wherein the second specified parameter may be a 0 voltage;

wherein the first preset condition indicates that the variation amplitude of the eye pupil is larger than a first preset value, and the second preset condition indicates that the variation amplitude of the eye pupil is larger than a second preset value.

Determining the variation amplitude of the eye pupil according to the eye pupil characteristic information may comprises: calculating a difference value between the value of the eye pupil characteristic information collected in the present cycle and the value of the eye pupil characteristic information collected in the previous cycle, and taking the difference value as the variation amplitude of the eye pupil.

As shown in FIGS. 5a and 5b, the light transmission module may comprise: a first layer light transmission part, first material, a second layer light transmission part. The first material may be liquid crystal, and may particularly comprise liquid crystal molecular coating layers 52 and liquid crystal molecules.

The arrangement direction of liquid crystal molecules in the liquid crystal may be changed according to the adjusted driving voltage, so as to adjust the polarization direction of the liquid crystal. Thus, the light transmittance and color of the light transmission module may be adjusted as shown in FIGS. 5a and 5b. In particular, electrodes of a liquid crystal panel are made of a metallic compound such as ITO, formed on both sides of a substrate made of the first material and etched by an etching process. The first layer light transmission part may comprise a first polarizer 55 and a first glass substrate 51. The second layer light transmission part may comprise a second polarizer 57 and a second glass substrate 53.

As shown in FIG. 5a, the arrangement of the liquid crystal molecules is a helical structure having an optical rotation activity for light. Polarization directions of the first polarizer 55 and the second polarizer 57 at the two sides are perpendicular with each other. When the voltage between the upper and the lower substrates is 0, only light in a direction identical with that of the first polarizer 55 may enter into the coating layer of the liquid crystal molecules in the helical structure after natural light 54 goes through the first polarizer 55. The direction of the incident light is rotated by 90° due to the optical rotation activity of the helical structure. Then, the rotated incident light is irradiated to the second polarizer 57 on the other end. Since the polarization directions of the two polarizers are perpendicular with each other, the incident light may completely go out through the polarizer at the other end, and thus completely enter into the user's eyes. The user may see a color of the first polarizer or the second polarizer. For example, when both the first polarizer and the second polarizer are transparent, the user may see the natural light.

As shown in FIG. 5b, when the voltage 56 between the first glass substrate 51 and the second glass substrate 53 is an alternating voltage, the helical structure of the liquid crystal molecules in the first material may become a syntropic arrangement under the effect of an electric (magnetic) field, and thus does not have any rotation on the direction of the light. Since the polarization directions of the first polarizer 55 and the second polarizer 57 are perpendicular with each other, the incident light cannot go out through the second polarizer 57, and no light 54 can enter into the user's eyes. The user may see a black color. As such, two basic bright and dark states of the liquid crystal display may be implemented by applying different alternating voltages across the electrodes of the upper and the lower glass substrates.

The light transmittance comprises a transmittance of at least one visible light, e.g., a transmittance of natural light.

A scenario in which the present embodiment is implemented will be described below.

The image of the specific area may be collected by the camera;

the human eye feature of the user, i.e., the diameter or radius or area of the pupil, may be collected according to the image of the specified area;

determining the variation amplitude of the eye pupil according to the eye pupil characteristic information;

determining that the first control strategy is increasing the driving voltage of the liquid crystal to the first specified parameter, when the variation amplitude of the eye pupil is zoom-in, and the zoom-in amplitude matches with the first preset condition;

changing the optical characteristics of the liquid crystal according to the first control strategy, and adjusting the optical parameters of the light transmission module by adjusting the optical characteristics of the first material.

Therefore, with the technical solution of the present embodiment, the first control strategy may be determined according to the human eye characteristic information of the user; the optical characteristics of the first material may be changed according to the first control strategy, and accordingly the optical parameters of the light transmission module may be adjusted. Thus, the sensitivity of the user's eyes to the light may be determined according to the situation of the user, so that the eyes of the user may obtain suitable light, and the use experience of the user may thus be improved.

Device Example Three

Figure 8:
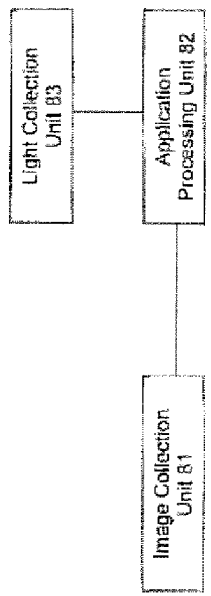
FIG. 8 is a second structure schematic diagram of a wearable electronic device according to an embodiment of the present disclosure.

An embodiment of the present disclosure provides a wearable electronic device, as shown in FIG. 8, comprising:

an image collection unit 81 connected to a fixed portion, the image collection unit being configured to collect human eye characteristic information of a user; the fixed portion being configured to maintain a relative position relationship between the wearable electronic device and a head of the user when the user wears the electronic device;

an application processing unit 82, configured to obtain the human eye characteristic information of the user collected by the image collection unit; determine a first control strategy according to the human eye characteristic information and a first preset rule; and change optical characteristics of first material according to the first control strategy, so as to adjust optical parameters of the light transmission module; wherein the light transmission module is connected to the fixed portion, and the light transmission module is provided with the first material.

Here, the wearable electronic device may be smart glasses. The fixed portion may be a frame of glasses.

The image collection unit 81 may be a camera.

The application processing unit 82 is particularly configured to control the image collection unit to collect eye pupil characteristic information of the user. The image collection unit periodically specifies an image in a specified area, collects eye pupil characteristic information of the user in the image of the specified area, as shown in FIG. 2, collects variation information of the pupil 21 of the user's eye. The periodicity may be set according to actual requirements, e.g. once per second. The eye pupil characteristic information may be a diameter, a radius, or an area of the pupil 21.

The application processing unit 82 is particularly configured to determine a variation amplitude of the eye pupil according to the eye pupil characteristic information; judge whether the variation amplitude of the eye pupil matches with a first preset condition; and determine that the first control strategy is to increase a driving voltage of the liquid crystal to a first specified parameter in the case that the variation amplitude of the eye pupil matches with the first preset condition, wherein the first specified parameter may be an alternating voltage;

determine the variation amplitude of the eye pupil according to the eye pupil characteristic information; judge whether the variation amplitude of the eye pupil matches with a second preset condition; and determine that the first control strategy is to decrease the driving voltage of the liquid crystal to a second specified parameter in the case that the variation amplitude of the eye pupil matches with the second preset condition, wherein the second specified parameter may be a 0 voltage;

wherein the first preset condition indicates that the variation amplitude of the eye pupil is larger than a first preset value, and the second preset condition indicates that the variation amplitude of the eye pupil is larger than a second preset value.

Determining the variation amplitude of the eye pupil according to the eye pupil characteristic information may comprises: calculating a difference value between the value of the eye pupil characteristic information collected in the present cycle and the value of the eye pupil characteristic information collected in the previous cycle, and taking the difference value as the variation amplitude of the eye pupil.

As shown in FIGS. 5a and 5b, the light transmission module may comprise: a first layer light transmission part, first material, a second layer light transmission part. The first material may be liquid crystal, and may particularly comprise liquid crystal molecular coating layers 52 and liquid crystal molecules.

The arrangement direction of liquid crystal molecules in the liquid crystal may be changed according to the adjusted driving voltage, so as to adjust the polarization direction of the liquid crystal. Thus, the light transmittance and color of the light transmission module may be adjusted as shown in FIGS. 5a and 5b. In particular, electrodes of a liquid crystal panel are made of a metallic compound such as ITO, formed on both sides of a substrate made of the first material and etched by an etching process. The first layer light transmission part may comprise a first polarizer 55 and a first glass substrate 51. The second layer light transmission part may comprise a second polarizer 57 and a second glass substrate 53.

As shown in FIG. 5a, the arrangement of the liquid crystal molecules is a helical structure having an optical rotation activity for light. Polarization directions of the first polarizer 55 and the second polarizer 57 at the two sides are perpendicular with each other. When the voltage between the upper and the lower substrates is 0, only light in a direction identical with that of the first polarizer 55 may enter into the coating layer of the liquid crystal molecules in the helical structure after natural light 54 goes through the first polarizer 55. The direction of the incident light is rotated by 90° due to the optical rotation activity of the helical structure. Then, the rotated incident light is irradiated to the second polarizer 57 on the other end. Since the polarization directions of the two polarizers are perpendicular with each other, the incident light may completely go out through the polarizer at the other end, and thus completely enter into the user's eyes. The user may see the color of the first polarizer or the second polarizer. For example, when both the first polarizer and the second polarizer are transparent, the user may see the natural light.

As shown in FIG. 5b, when the voltage 56 between the first glass substrate 51 and the second glass substrate 53 is an alternating voltage, the helical structure of the liquid crystal molecules in the first material may become a syntropic arrangement under the effect of an electric (magnetic) field, and thus does not have any rotation on the direction of the light. Since the polarization directions of the first polarizer 55 and the second polarizer 57 are perpendicular with each other, the incident light cannot go out through the second polarizer 57, and no light 54 can enter into the user's eyes. Then the user may see a black color. As such, two basic bright and dark states of the liquid crystal display may be implemented by applying different alternating voltages across the electrodes of the upper and the lower glass substrates.

The application processing unit 82 is particularly configured to adjust the driving voltage of the liquid crystal according to the first control strategy; and change an arrangement direction of liquid crystal molecules in the liquid crystal according to the adjusted driving voltage, so as to adjust a polarization direction of the liquid crystal, and thus to adjust a light transmittance and color of the light transmission module.

The light transmittance comprises a transmittance of at least one visible light, e.g., a transmittance of natural light.

Preferably, the wearable electronic device further comprises a light collection unit 83 arranged on the fixed portion, configured to collect light information of an environment where the wearable electronic device is located.

Accordingly, the application processing unit 82 is further configured to: obtain the light information, collected by the light collection unit, of the environment where the wearable electronic device is located; and determine the first control strategy according to the human eye characteristic information, the light information and the first preset rule.

In particular, the application processing unit 82 is particularly configured to obtain brightness or color of the light information. The application processing unit 82 determines that the first control strategy is to refrain from adjusting the driving voltage according to the brightness of the light information and the first preset rule, if the brightness of the light information is lower than a preset brightness value.

If the brightness of the light information is no lower than the preset brightness value, the application processing unit 82 determines the variation amplitude of the eye pupil according to the eye pupil characteristic information; judges whether the variation amplitude of the eye pupil matches with the first preset condition; and determines that the first control strategy is increasing the driving voltage of the liquid crystal to the first specified parameter in the case that the variation amplitude of the eye pupil matches with the first preset condition;

The application processing unit 82 determines the variation amplitude of the eye pupil according to the eye pupil characteristic information; judges whether the variation amplitude of the eye pupil matches with the second preset condition; and determines that the first control strategy is decreasing the driving voltage of the liquid crystal to the second specified parameter, in the case that the variation amplitude of the eye pupil matches with the second preset condition;

The first preset condition indicates that the variation amplitude of the eye pupil is larger than the first preset value, and the second preset condition indicates that the variation amplitude of the eye pupil is larger than the second preset value.

Alternatively, the application processing unit 82 is particularly configured to: determine that the first control strategy is to refrain from adjusting the driving voltage according to the brightness of the light information and the first preset rule, if the color of the light information satisfies a specified color value.

If the color of the light information does not satisfy a specified color value, the application processing unit 82 is configured to: determine the variation amplitude of the eye pupil according to the eye pupil characteristic information; judge whether the variation amplitude of the eye pupil matches with the first preset condition; and determine that the first control strategy is to increase the driving voltage of the liquid crystal to the first specified parameter, in the case that the variation amplitude of the eye pupil matches with the first preset condition.

If the color of the light information does not satisfy a specified color value, the application processing unit 82 is also configured to: determine the variation amplitude of the eye pupil according to the eye pupil characteristic information; judging whether the variation amplitude of the eye pupil matches with the second preset condition; and determining that the first control strategy is decreasing the driving voltage of the liquid crystal to the second specified parameter, in the case that the variation amplitude of the eye pupil matches with the second preset condition;

In this case, the first preset condition indicates that the variation amplitude of the eye pupil is larger than the first preset value, and the second preset condition indicates that the variation amplitude of the eye pupil is larger than the second preset value.

As such, it may be guaranteed that the user can obtain the largest amount of light when the surrounding light is weaker.

Figure 9:
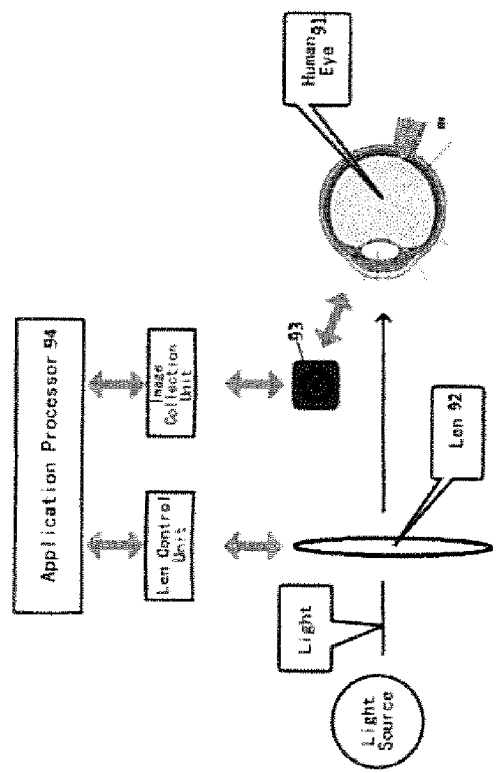
FIG. 9 is a schematic diagram of an application scenario according to an embodiment of the present disclosure.

Hereinafter, an application scenario according to an embodiment of the present disclosure is provided. As shown in FIG. 9, when the human eye 91 is stimulated by variation of light, the eye pupil may change. For example, when the brightness of a light source becomes stronger, the pupil may zoom out; and when the brightness of the light source becomes weaker, the pupil may zoom in.

An image collection unit 93 may collect an image of the human eye 91 periodically. An application processing unit 94 may obtain human eye characteristic information in the collected image of the human eye 91, and determine a pupil feature, such as a diameter, or radius or area of the pupil, according to the human eye characteristic information.

The application processing unit 94 may determine a first control strategy according to the human eye characteristic information and a first preset rule, e.g. determining a variation amplitude of the eye pupil according to the eye pupil characteristic information; judging whether the variation amplitude of the eye pupil matches with a first preset condition; and determining that the first control strategy is to increase a driving voltage of the liquid crystal to a first specified parameter in the case that the variation amplitude of the eye pupil matches with the first preset condition, wherein the first specified parameter may be an alternating voltage; determining the variation amplitude of the eye pupil according to the eye pupil characteristic information; judging whether the variation amplitude of the eye pupil matches with a second preset condition; and determining that the first control strategy is to decrease the driving voltage of the liquid crystal to a second specified parameter in the case that the variation amplitude of the eye pupil matches with the second preset condition, wherein the second specified parameter may be a 0 voltage.

The optical characteristics of the liquid crystal may be changed according to the first control strategy, so as to adjust the optical parameters of the light transmission module 92.

Therefore, with the technical solution of the present embodiment, the first control strategy may be determined according to the human eye characteristic information of the user; the optical characteristics of the first material may be changed according to the first control strategy, and accordingly the optical parameters of the light transmission module may be adjusted. Thus, the sensitivity of the user's eyes to the light may be determined according to the situation of the user, so that the eyes of the user may obtain suitable light, and the use experience of the user may thus be improved.

It can be appreciated from the embodiments of the present application that the disclosed device and method can be implemented in alternative ways. The device embodiments as described above are illustrative only. For example, while the units have been divided in accordance with their logical functions, other divisions are possible in practice. For example, more than one unit or element can be combined or can be integrated into another system, or some features can be ignored or omitted. In addition, the coupling, direct coupling or communicative connection between various components as shown or discussed can be an indirect coupling or communicative connection via some interface, device or unit and can be electrical, mechanical or in another form.

The units described above as separated may or may not be physically separated. The components shown as units may or may not be physical units. They can be co-located or can be distributed over a number of network elements. Depending on actual requirements, some or all of the units can be selected to achieve the object of the present disclosure.

Further, all the functional units in various embodiments of the present disclosure can be integrated within one processing unit, or each of these units can be a separate unit, or two or more units can be integrated into one unit. Such integrated unit can be implemented in hardware, possibly in combination with software functional units.

As will be understood by the skilled in the art, all or parts of steps in the above method embodiments may be implemented by hardware related to program instructions, and the above programs may be stored in a computer readable storage medium. When executed, the program may perform steps in the above method embodiments. The above storage medium comprises various media capable of storing program codes, such as a mobile storage device, a read-only memory (ROM), a random access memory (RAM), a magnetic disc or an optical disc and the like.

While the embodiments of the present disclosure have been described above, the scope of the present disclosure is not limited thereto. Various modifications and alternatives can be made by those skilled in the art without departing from the scope of the present disclosure. These modifications and alternatives are to be encompassed by the scope of the present disclosure which is only defined by the claims as attached.

What is claimed is:

1. An information processing method performed in a wearable electronic device:
periodically acquiring an eye pupil size of a user wearing the wearable electronic device using an image collection device;
calculating a difference between the eye pupil size acquired in a current cycle and the eye pupil size acquired in a previous cycle using a processor; and
adjusting optical characteristics of a light transmission module of the wearable electronic device according to the calculated difference between the eye pupil size acquired in a current cycle and the eye pupil size acquired in a previous cycle;
wherein the light transmission module comprises a liquid crystal; and
wherein adjusting the optical characteristics of a light transmission module of the wearable electronic device further comprises:
adjusting a driving voltage of the liquid crystal according to the calculated difference between the eye pupil size acquired in a current cycle and the eye pupil size acquired in a previous cycle.

2. The method according to claim 1, wherein adjusting the driving voltage of the liquid crystal further comprising:
changing an arrangement direction of liquid crystal molecules in the liquid crystal, so as to adjust a polarization direction of the liquid crystal, and thus to adjust a light transmittance and color of the light transmission module.

3. The method according to claim 2, wherein the light transmittance comprises a transmittance of at least one visible light.

4. The method according to claim 3, further comprising:
refraining from a new adjustment of the optical characteristic of the light transmission module of the wearable electronic device, if an elapsed time since the last adjustment does not exceed a preset time.

5. The method according to claim 1, further comprising:
sensing a level of an ambient light around the wearable electronic device; and
refraining from a new adjustment of the optical characteristic of the light transmission module of the wearable electronic device, if the level of an ambient light around the wearable electronic device is lower than a present level of an ambient light around the wearable electronic device.

6. A wearable electronic device, comprising:
a fixed portion, wherein the fixed portion is to be mounted on a head of a user;
an image collection device disposed on the fixed portion, wherein the image collection device is configured to obtain an eye pupil size of the user; and
a light transmission module disposed on the fixed portion, wherein an optical characteristic of the light transmission module changes based on the eye pupil size of the user;
wherein the light transmission module is a lens comprising:
a first layer made of a first material, wherein the first material is a liquid crystal, and wherein the first layer has a first polarizer and a first glass substrate; and
a second layer made of the first material, wherein the second layer has a second polarizer and a second glass substrate.

7. The wearable electronic device according to claim 6, wherein the image collection device is a camera.

8. The wearable electronic device according to claim 6, wherein the image collection device further comprises an application processor.

9. The wearable electronic device according to claim 8, wherein the application processor controls a light transmittance of the light transmission module and the light transmittance of the light transmission module comprises a transmittance of at least one visible light.

10. The wearable electronic device according to claim 6, wherein the fixed portion is a frame of glasses.

11. The wearable electronic device according to claim 6, wherein the wearable electronic device further comprises a light collection device arranged on the fixed portion.

* * * * *